United States Patent [19]

Molloy et al.

[11] Patent Number: 4,504,467
[45] Date of Patent: Mar. 12, 1985

[54] GLYCOPEPTIDE DERIVATIVES

[75] Inventors: R. Michael Molloy, Danville; Manuel Debono, Indianapolis, both of Ind.

[73] Assignee: Eli Lilly and Company, Indianapolis, Ind.

[21] Appl. No.: 544,339

[22] Filed: Oct. 21, 1983

[51] Int. Cl.³ .................. A01N 25/00; C07C 103/52; A61K 37/00
[52] U.S. Cl. .......................... 424/118; 260/112.5 R; 514/8
[58] Field of Search ................ 260/112.5 R; 424/118, 424/177

[56] References Cited

U.S. PATENT DOCUMENTS

| | | | |
|---|---|---|---|
| 2,990,329 | 6/1961 | Philip et al. | 167/65 |
| 3,928,571 | 12/1975 | Raun | 424/118 |
| 4,029,769 | 6/1977 | Debono | 424/118 |
| 4,115,552 | 9/1978 | Hamill et al. | 424/118 |
| 4,122,168 | 10/1978 | Michel et al. | 424/118 |
| 4,322,343 | 3/1982 | Debono | 260/112.5 R |
| 4,322,406 | 3/1982 | Debono et al. | 424/118 |

OTHER PUBLICATIONS

Donald G. Lee, "Oxidation of Oxygen and Nitrogen Containing Functional Groups with Transition Metal Compounds," in *Oxidation*, vol. I, edited by Robert L. Augustine 1969, Marcel Dekker, Inc., New York, p. 98.

R. B. Kelly, "Phenylhydrazide as a Protective Group in Peptide Synthesis. The Oxidation of γ-Phenylhydrazides of N–Carbobenzoxyγ-L–Glutamylamino Acid Esters with Manganese Dioxide," *J. Org. Chem.* 28, 453–456 (1963).

R. B. Kelly et al., "The Oxidation of Phenylhydrazides to Carboxylic Acids with Manganese Dioxide. II. By Products," *J. Org. Chem.* 29, 1273–1275 (1964).

H. B. Henbest and A. Thomas, "Amine Oxidation. Part I. The Side Chain Oxidation of N–Alkyl- and NN–Dialkyl–Anilines by Manganese Dioxide," *J. Chem. Soc.* 3032–3039 (1957).

D. H. Williams et al., "Structure of Ristocetin A," *J. C. S. Chem. Com.* 1979, 906–908.

*Primary Examiner*—Delbert R. Phillips
*Attorney, Agent, or Firm*—Nancy J. Harrison; Arthur R. Whale

[57] ABSTRACT

Method of preparing compounds of formula 1:

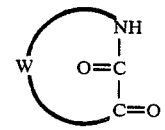

by oxidative deamination of a glycopeptide antibiotic of formula 2:

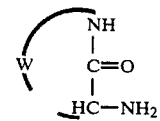

the antibiotic being selected from A35512 factors A, B, C, E and H, A35512B pseudoaglycone, actaplanin factors A, $B_1$, $B_2$, $B_3$, $C_{1a}$, $C_{2a}$, $C_3$, $D_1$, $D_2$, $E_1$, G, K, L, M, N and O, actaplanin pseudoaglycone, A41030 factors A, B, C, D, E, F and G, A47934, ristocetin A and ristocetin A pseudoaglycone, novel compounds and compositions and methods of increasing feed-utilization efficiency in animals are provided.

21 Claims, No Drawings

GLYCOPEPTIDE DERIVATIVES

SUMMARY OF THE INVENTION

This invention relates to novel glycopeptide derivatives and to a method of making such derivatives by oxidative deamination. In the compounds prepared by this process an amino group in the glycopeptide antibiotic is replaced by a carbonyl group. The new derivatives retain the gram-positive antibacterial activity characteristic of this class of antibiotics and may be useful intermediates to other new antibiotics. The new derivatives should also increase feed-utilization efficiency and enhance milk production in ruminants.

DETAILED DESCRIPTION

The oxidatively-deaminated glycopeptide antibiotics prepared by the process of this invention are compounds of formula 1:

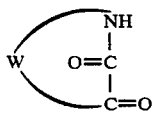

1 wherein W represents the remaining portion of a glycopeptide antibiotic of formula 2:

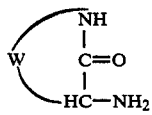

2 and the antibiotic is selected from A35512 factors A, B, C, E and H, A35512B pseudoaglycone, actaplanin factors A, $B_1$, $B_2$, $B_3$, $C_{1a}$, $C_{2a}$, $C_3$, $D_1$, $D_2$, $E_1$, G, K, L, M, N and O, actaplanin pseudoaglycone, A41030 factors A, B, C, D, E, F and G, A47934, ristocetin A and ristocetin A pseudoaglycone. The compounds of formula 3:

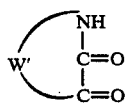

3 wherein W' represents the remaining portion of a glycopeptide antibiotic of formula 4:

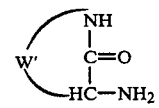

4 the formula 4 antibiotic being selected from A35512 factors A, B, C, E and H, A35512B pseudoaglycone, A41030 factors A, B, C, D, E, F and G, A47934, ristocetin A and ristocetin A pseudoaglycone are also part of this invention.

The compound of formula 1 wherein the glycopeptide residue is that of actaplanin factor A is the subject of a copending application of LaVerne D. Boeck, Gladys M. Clem, Charles L. Hershberger, Marie T. Anderson and Karl H. Michel entitled GLYCOPEPTIDE COMPOUND CUC/CSV AND PROCESS FOR ITS PRODUCTION, Ser. No. 544,338, filed herewith this even date; and the compounds of formula 1 wherein the glycopeptide residue is selected from actaplanin factors $B_1$, $B_2$, $B_3$, $C_{1a}$, $C_{2a}$, $C_3D_1$, $D_2$, $E_1$, G, K, L, M, N and O and the actaplanin pseudoaglycone are the subject of copending application of Gladys M. Clem, LaVerne D. Boeck, Marie T. Anderson and Karl H. Michel entitled GLYCOPEPTIDE BIOCONVERSION PRODUCTS, Ser. No. 544,332, also filed herewith this even date.

The process of this invention provides, in one step, a selective modification of a chemically complex substrate, i.e., certain glycopeptide antibiotics. Such a modification was heretofore not available by chemical methods. The glycopeptide derivatives produced by the process of this invention and their salts retain the gram-positive antibacterial activity characteristic of this group of antibiotics and are, therefore, valuable additions to the antibiotics available in this class.

In addition, this invention relates to methods of increasing feed-utilization efficiency and promoting growth in animals and improving milk production in lactating ruminants and to pharmaceutical compositions comprising a formula 3 compound and a suitable carrier.

New antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half life, and more advantageous rate or route of excretion and rate or pattern of metabolism) are some of the goals for improved antibiotics.

The parent antibiotics used as starting materials in the process of this invention are all members of the group of glycopeptide antibiotics. Antibiotic A35512 factors A, B, C, E and H are described by Karl H. Michel and Calvin E. Higgens in U.S. Pat. No. 4,122,168, issued Oct. 24, 1978; and A35512B pseudo ($\psi$)aglycone is described by Manuel Debono in U.S. Pat. No. 4,029,769, issued June 14, 1977 (note: in the patent, this compound is called A35512B aglycone, but will be called A35512B $\psi$aglycone herein since it retains the amino-sugar). Actaplanin (antibiotic A-4696) factors A and B are described by Hamill et al. in U.S. Pat. No. 4,115,552, issued Sept. 19, 1978. Actaplanin factors $B_1$, $B_2$, $B_3$, $C_{1a}$, $C_3$ and $E_1$ are described by Debono et al. in U.S. Pat. No. 4,322,406, issued Mar. 30, 1982. The actaplanin pseudo-aglycone is described by Debono in U.S. Pat. No. 4,029,769, issued Mar. 30, 1982. Actaplanin factor G is described by Hershberger et al. in U.S. Pat. No. 4,462,942, July 31, 1984; and actaplanin factors K, L, M, N and O are described by Hunt et al. in an allowed co-pending application, Ser. No. 488,967, filed Apr. 27, 1983. A41030 factors A, B, C, D, E, F and G are described in the co-pending application of Michel et al., Ser. No. 443,496, filed Nov. 22, 1982; and A47934 is described by Hamill et al., in U.S. Pat. No. 4,461,723, issued July 24, 1984. Ristocetin A preparation is described by Philip et al. in U.S. Pat. No. 2,990,329, issued June 27, 1961. Ristocetin ψaglycone is prepared as described by Williams et al in *J. C. S. Chem. Comm.* 1979, 906–908 (see esp. p. 907).

The structures of A35512B and its ψaglycone are shown in formulas 5a and 5b:

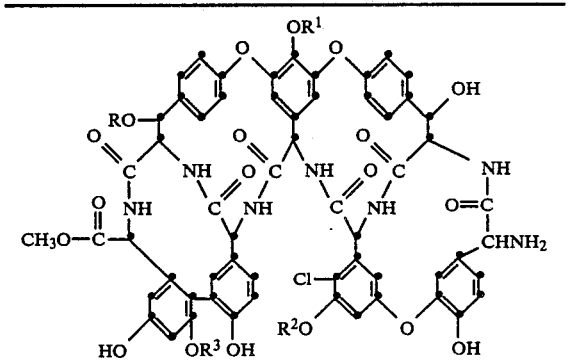

| Group | A35512B (5a) | A35512B ψAglycone (5b) |
|---|---|---|
| R | 3-epi-L-vancosaminyl | 3-epi-L-vancosaminyl |
| $R^1$ | rhamnosyl-glucosyl | H |
| $R^2$ | fucosyl | H |
| $R^3$ | mannosyl | H |

Thus, the new A35512B derivatives of this invention have formulas 6a and 6b:

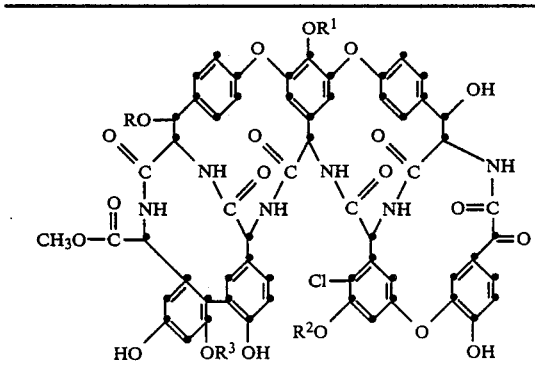

6

| Group | A35512B MnO$_2$ Product (6a) | A35512B ψAglycone MnO$_2$ Product (6b) |
|---|---|---|
| R | 3-epi-L-vancosaminyl | 3-epi-L-vancosaminyl |
| $R^1$ | rhamnosyl-glucosyl | H |
| $R^2$ | fucosyl | H |

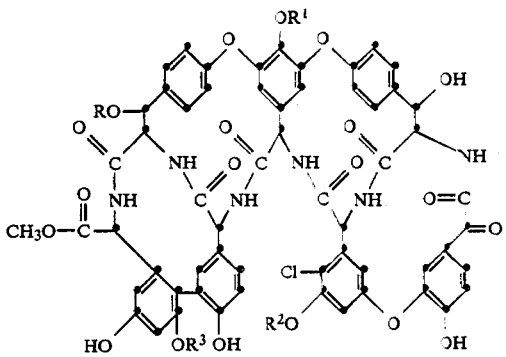

| Group | A35512B MnO$_2$ Product (6a) | A35512B ψAglycone MnO$_2$ Product (6b) |
|---|---|---|
| $R^3$ | mannosyl | H |

The remaining A35512 factors A, C, E and H have not been completely characterized, but each contains the

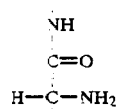

moiety and each will, therefore, react in a similar manner to form the corresponding

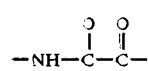

containing MnO$_2$ products.

The structure of ristocetin A and its pseudoaglycone are shown in formulas 7a and 7b:

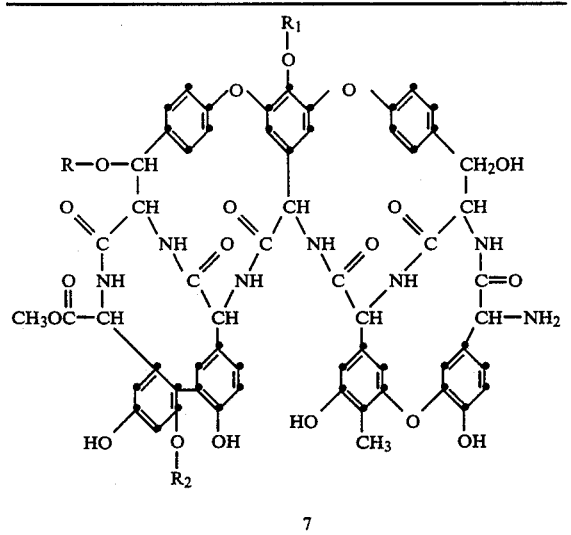

7

| Group | Ristocetin A (7a) | Ristocetin A ψAglycone (7b) |
|---|---|---|
| R | ristosaminyl | ristosaminyl |
| $R_1$ | O—β-D-arabinopyranosyl-(1→2)-O—α-D-mannopyranosyl-(1→2)-O—α-L-rhamnopyranosyl-(1→6)-O—β-D-glucopyranosyl | H |
| $R_2$ | mannosyl | H |

Thus, the new ristocetin A derivatives of this invention have formulas 8a and 8b:

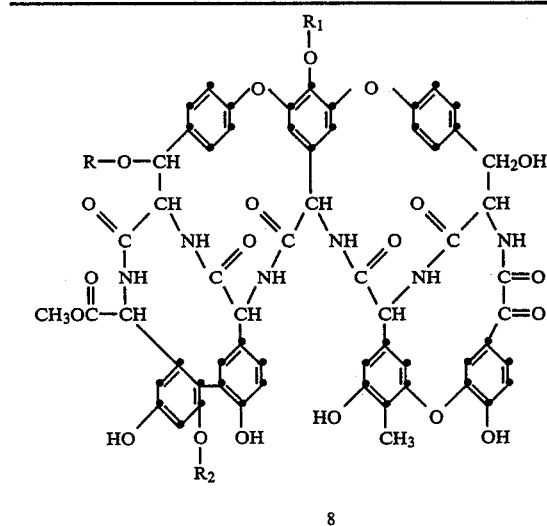

8

| Group | Ristocetin MnO$_2$ Product (8a) | Ristocetin Pseudoaglycone MnO$_2$ Product (8b) |
|---|---|---|
| R | ristosaminyl | ristosaminyl |
| $R_1$ | O—β-D-arabinopyranosyl-(1→2)-O—α-D-mannopyranosyl-(1→2)-O—α-L-rhamnopyranosyl-(1→6)-O—β-D-glucopyranosyl | H |
| $R_2$ | mannosyl | H |

The structure of A47934 is shown in formula 9:

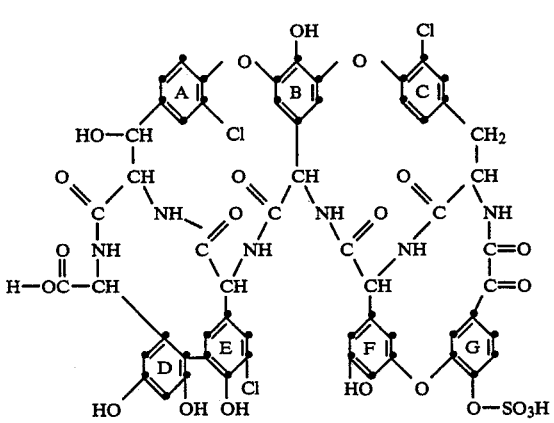

9

Thus, the new A47934 derivative of this invention has formula 10:

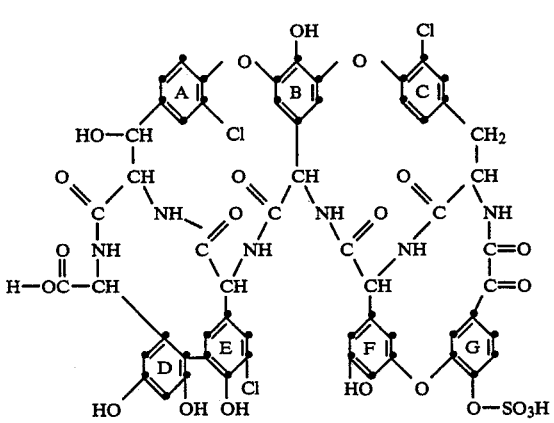

10

The structures of A41030 factors A, B, C, D, E and F are shown in formulas 11a–11g.

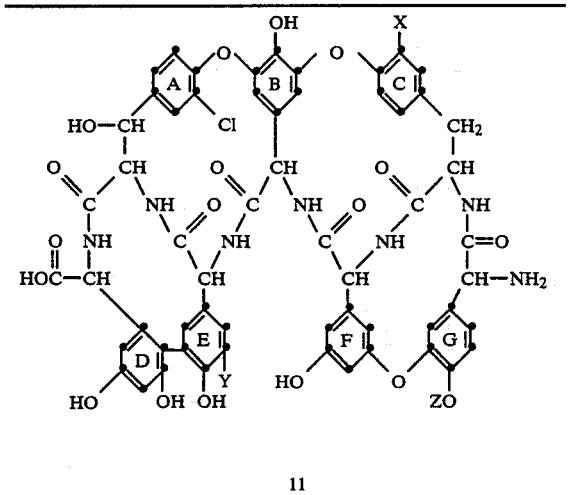

11

| Formula | A41030 | X | Y | Z |
|---|---|---|---|---|
| 11a | A | Cl | Cl | H |
| 11b | B | Cl | H | H |
| 11c | C | Cl | Cl | galactosyl |
| 11d | D[a] | H | Cl | H |
| 11e | E | H | H | H |
| 11f | F | Cl | Cl | galactosyl-galactosyl |
| 11g | G[a] | Cl | Cl | galactosyl-galactosyl |

[a]Factors D and G have two equivalent n-butyl groups attached to the peptide nucleus at an undetermined location.

Thus, the new A41030 derivatives of this invention have formulas 12a–12g:

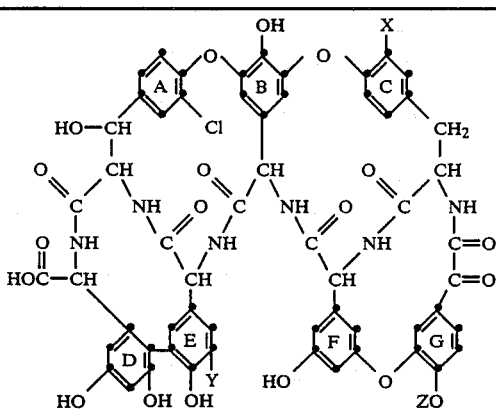

12

| Formula | A41030 MnO$_2$ Product | X | Y | Z |
|---|---|---|---|---|
| 12a | A | Cl | Cl | H |
| 12b | B | Cl | H | H |
| 12c | C | Cl | Cl | galactosyl |
| 12d | D[a] | H | Cl | H |
| 12e | E | H | H | H |
| 12f | F | Cl | Cl | galactosyl-galactosyl |
| 12g | G[a] | Cl | Cl | galactosyl-galactosyl |

[a]see footnote to formulas 11d and 11g

The actaplanin factors and pseudoaglycone used in the process of this invention have the structures shown in formulas 13a–13p:

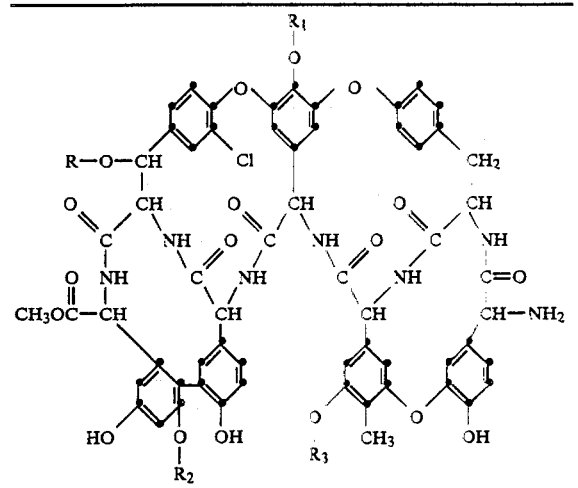

13

| Formula | Actaplanin | $R_1$ | $R_2$ | $R_3$ |
|---|---|---|---|---|
| 13a | A | mannosyl-glucosyl | mannosyl | mannosyl |
| 13b | $B_1$ | rhamnosyl-glucosyl | mannosyl | mannosyl |
| 13c | $B_2$ | glucosyl | mannosyl | mannosyl |
| 13d | $B_3$ | mannosyl-glucosyl | mannosyl | H |
| 13e | $C_{1a}$ | rhamnosyl-glucosyl | mannosyl | H |
| 13f | $C_{2a}$ | H | mannosyl | mannosyl |
| 13g | $C_3$ | glucosyl | H | mannosyl |
| 13h | $D_1$ | H | mannosyl | H |
| 13i | $D_2$ | H | H | mannosyl |
| 13j | G | glucosyl | mannosyl | H |
| 13k | K | mannosyl-glucosyl | H | mannosyl |
| 13m | L | rhamnosyl-glucosyl | H | mannosyl |
| 13n | M | mannosyl-glucosyl | H | H |
| 13o | N | rhamnosyl-glucosyl | H | H |
| 13p | O | glucosyl | H | H |
| 13q | ψaglycone | H | H | H |

Thus, the actaplanin derivatives prepared by the process of this invention have formulae 14a–14p.

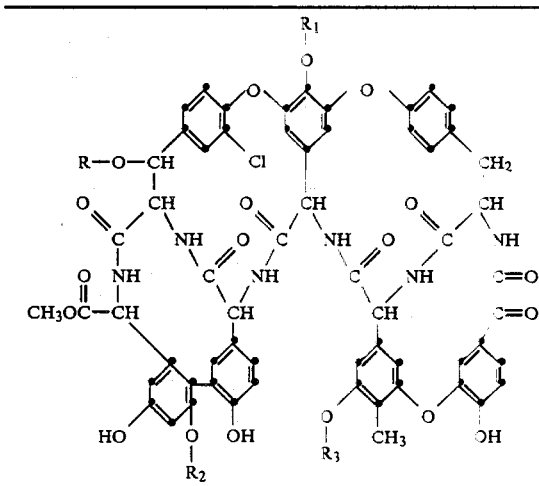

14

| Formula | Actaplanin MnO$_2$ Product | $R_1$ | $R_2$ | $R_3$ |
|---|---|---|---|---|
| 14a | A | mannosyl-glucosyl | mannosyl | mannosyl |
| 14b | $B_1$ | rhamnosyl-glucosyl | mannosyl | mannosyl |
| 14c | $B_2$ | glucosyl | mannosyl | mannosyl |

-continued

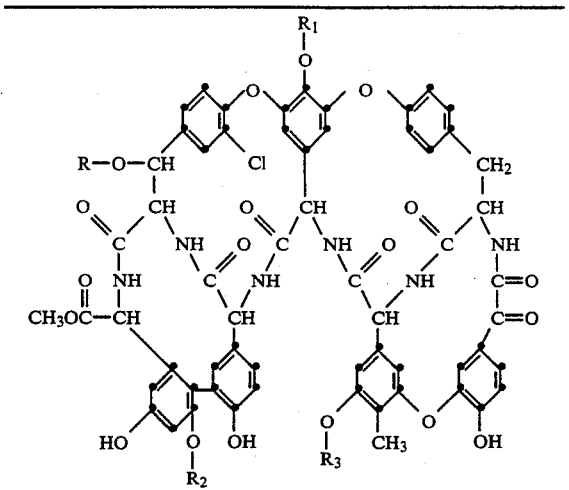

14

| Formula | Actaplanin MnO2 Product | R1 | R2 | R3 |
|---|---|---|---|---|
| 14d | B3 | mannosyl-glucosyl | mannosyl | H |
| 14e | C1a | rhamnosyl-glucosyl | mannosyl | H |
| 14f | C2a | H | mannosyl | mannosyl |
| 14g | C3 | glucosyl | H | mannosyl |
| 14h | D1 | H | mannosyl | H |
| 14i | D2 | H | H | mannosyl |
| 14j | G | glucosyl | mannosyl | H |
| 14k | K | mannosyl-glucosyl | H | mannosyl |
| 14m | L | rhamnosyl-glucosyl | H | mannosyl |
| 14n | M | mannosyl-glucosyl | H | H |
| 14o | N | rhamnosyl-glucosyl | H | H |
| 14p | O | glucosyl | H | H |
| 14q | ψaglycone | H | H | H |

The process of this invention comprises treating a glycopeptide antibiotic of formula 2 in a suitable solvent in the presence of a sufficient amount of oxidizing agent to deaminate the

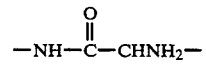

portion of the antibiotic. Polar aprotic solvents such as dimethylformamide are suitable solvents for the process of this invention. A preferred oxidizing agent for the process is manganese dioxide. Other oxidizing agents which should be useful for this reaction include potassium permanganate and a combination of t-butylhypochlorite and sodium bicarbonate. The temperature of the reaction is not critical, but room temperature is usually preferred for the reaction. The reaction time will vary, depending on a number of factors, such as the starting antibiotic, the oxidizing agent used and the temperature of the reaction. The reaction is conveniently monitored by thin-layer chromatography (TLC) to determine the reaction time. The reaction product is isolated using purification procedures which are recognized in the art.

The new compounds of this invention, i.e. the compounds of formulas 3, 6, 8, 10 and 12 form salts, particularly acid addition salts. These salts are also useful as antibiotics and are a part of this invention. In another aspect, such salts are useful as intermediates, for example, for separating and purifying the derivatives. Salts which are pharmaceutically acceptable are especially preferred.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

The derivatives prepared by the method of this invention inhibit the growth of pathogenic bacteria, especially gram-positive bacteria. The minimal inhibitory concentrations (MIC's) at which illustrative comounds inhibit certain bacteria are given in Table I. The MIC's in Table I were determined by standard agar-dilution assays.

TABLE I

| | Antibiotic Activity of Formula 1 Derivatives[a] | | | | |
|---|---|---|---|---|---|
| | Test Compound[b] | | | | |
| Test Organism | A35512B MnO2 Product | A4696A MnO2 Product | A4696G MnO2 Product | A41030A MnO2 Product | A41030B MnO2 Product |
| Staphylococcus aureus X1.1 | 4 | 4 | 1 | 0.06 | 0.125 |
| Staphylococcus aureus V41[c] | 8 | 4 | 1 | 0.125 | 0.125 |
| Staphylococcus aureus X400[d] | 8 | 8 | 2 | 0.25 | 0.25 |
| Staphylococcus aureus S13E | 4 | 4 | 1 | 0.125 | 0.125 |
| Staphylococcus epidermidis EPI1 | 8 | 16 | 1 | 0.125 | 0.06 |
| Staphylococcus epidermidis EPI2 | 8 | 8 | 0.5 | — | 0.25 |
| Streptococcus pyogenes C203 | 2 | 0.5 | 0.25 | 0.25 | 0.5 |
| Streptococcus pneumoniae Park I | 2 | 1 | 0.25 | 0.25 | 0.25 |
| Streptococcus Group D X66 | 16 | 4 | 1 | 1 | 1 |
| Streptococcus Group 9960 | 4 | 16 | 0.5 | 1 | 2 |
| Haemophilus influenzae C.L.[e] | >128 | —[g] | — | 8 | 8 |
| Haemophilus influenzae 76[f] | >128 | — | — | 4 | 8 |

[a]MIC in mcg/ml
[b]Compound numbers = Example numbers
[c]Penicillin-resistant strain
[d]Methicillin-resistant strain
[e]Ampicillin-sensitive strain
[f]Ampicillin-resistant strain
[g]Not tested The derivatives prepared by the method of this invention have shown in vivo antimicrobial activity against experimentally-induced infections in laboratory animals. When two doses of test compound were administered to experimentally infected mice, the activity observed was measured as an $ED_{50}$ value [effective dose in mg/kg to protect 50% of the test animals: see Warren Wick, et al., *J. Bacteriol.* 81, 233-235 (1961)]. $ED_{50}$ values observed for illustrative compounds are given in Table II.

TABLE II $ED_{50}$ Values of Formula I Compounds in Experimental Infections in Mice

| Test Compound | $ED_{50}$ Value[a] | | |
|---|---|---|---|
| | Staphylococcus aureus | Streptococcus pyogenes | Streptococcus pneumoniae |
| A35512B $MnO_2$ Product | 3.15 | 3.54 | 2.18 |
| A4696A $MnO_2$ Product | 1.59 | 1.09 | 0.84 |
| A4696G $MnO_2$ Product | 0.75 | 0.88 | <0.625 |
| A41030A $MnO_2$ Product | <0.62 | 7.49 | 6.4 |
| A41030B $MnO_2$ Product | <0.19 | >10. | 7.94 |

This invention also relates to a method of controlling bacterial infections. In carrying out the method of this invention, an effective amount of a compound of formula 3 is administered parenterally or orally or an infected or susceptible warm-blooded animal. The compound can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from 1 to about 300 mg/kg and preferably will be in the range of from about 1 to about 100 mg/kg. Suitable dosage regiments can be constructed.

In another aspect, this invention relates to compositions useful for the control of bacterial infections. These compositions comprise a compound of formula 3 together with a suitable vehicle. Compositions may be formulated for parenteral or oral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antiforms, sorbitol, and sugars can be useful suspending agents.

In another embodiment, this invention relates to methods of increasing feed-utilization efficiency and promoting growth rates in animals such as poultry, swine, sheep and cattle and of enhancing milk production in ruminants. In increasing feed utilization efficiency and promoting growth, a formula 3 compound is administered orally in a suitable feed in an amount of from about 2 to about 200 grams per ton of total feed. In enhancing milk production in ruminant, oral administration of a daily amount of from about 0.1 to about 10 mg/kg of body weight (or about 100 to 1600 mg/ruminant/day) is suggested.

Often the most practical way to administer the compounds is by formulation into the feed supply or drinking water. A variety of feeds, including the common dry feeds, liquid feeds, and pelleted feeds, may be used.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals of poultry will depend upon the amount of drug to be administered. The common methods of formulating, mixing, and pelleting feeds may be used to prepare feeds containing a compound of formula 3.

In order to illustrate more fully the operation of this invention, the following examples are provided.

EXAMPLE 1

Preparation of A35512B $MnO_2$ Oxidized Product (Compound 6a)

A35512B.2HCl (2.0 g, 0.989 mMoles) was dissolved in DMF (160 ml) at room temperature. Activated manganese dioxide (8 g, 4 equivalents) was added. The black suspension which formed was allowed to stir at room temperature for 84 hours. Filtration through a pad of Hyflo Super-Cel twice gave a nearly colorless filtrate. The filtrate was concentrated under vacuum to give a cream-colored gum. The gum was triturated twice with diethyl ether (100 ml) and dried under vacuum to give 1.93 g of a foamy glass. This material was chromatographed over a reversed-phase C-18 silica-gel column, using a Waters Prep-500 Unit. A linear gradient of CH$_3$OH/H$_2$O containing 0.1% pyridinium acetate (from 1:4 to 1:1) was used for elution. Fractions of from 40-250 ml were collected, monitoring by silica-gel TLC (Merck S.G. plates), using a CHCl$_3$:CH$_3$OH:NH$_4$OH (2:3:1) solvent system. Fractions containing the desired component were combined and lyophilized to give 650 mg of compound 6a (32.5% yield).

EXAMPLES 2-7

Using the general procedure of Example 1, the following MnO$_2$ oxidation products were prepared:
Actaplanin factor A MnO$_2$ product (Compound 14a)
Actaplanin factor G MnO$_2$ product (Compound 14j)
Actaplanin pseudoaglycone MnO$_2$ product (Compound 14q)
A41030 factor A MnO$_2$ product (Compound 12a)
A41030 factor B MnO$_2$ product (Compound 12b)
A47934 MnO$_2$ product (Compound 10)

EXAMPLES 8-16

The following MnO$_2$ oxidation products can be prepared using the general procedure of Example 1:
Actaplanin factors B$_1$, B$_2$, B$_3$, C$_{1a}$, C$_3$ and D$_1$ MnO$_2$ products (Compounds 14b, 14c, 14d, 14e 14 g and 14h)
ristocetin A MnO$_2$ Product (Compound 8a)
ristocetin A pseudoaglycone MnO$_2$ Product (Compound 8b)
A35512B pseudoaglycone MnO$_2$ Product (Compound 6b)

We claim:

1. A process for preparing a compound of formula 1:

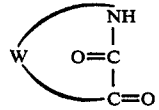

1 wherein W represents the remaining portion of a glycopeptide antibiotic of formula 2:

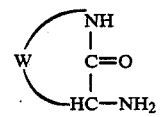

2 and the antibiotic is selected from A35512 factors A, B, C, E and H, A35512B pseudoaglycone, actaplanin factors A, B$_1$, B$_2$, B$_3$, C$_{1a}$, C$_{2a}$, C$_3$, D$_1$, D$_2$, E$_1$, G, K, L, M, N and O, actaplanin pseudoaglycone, A41030 factors A, B, C, D, E, F and G, A47934, ristocetin A and ristocetin A pseudoaglycone, which comprises reacting the antibiotic in a polar aprotic solvent in the presence of an oxidizing agent until the antibiotic is diaminated to give the formula 1 compound.

2. The process of claim 1 wherein the oxidizing agent is manganese dioxide.

3. The process of claim 1 wherein the antibiotic of formula 2 is A47934.

4. The process of claim 1 wherein the antibiotic of formula 2 is selected from A35512B factors A, B, C, E and H and A35512B pseudoaglycone.

5. The process of claim 1 wherein the antibiotic of formula 2 is selected from actaplanin factors A, B$_1$, B$_2$, B$_3$, C$_{1a}$, C$_{2a}$, C$_3$D$_1$, D$_2$, E$_1$, G, K, L, M, N and O and actaplanin pseudoaglycone.

6. The process of claim 1 wherein the antibiotic of formula 2 is selected from A41030 factors A, B, C, D, E, F and G.

7. The process of claim 1 wherein the antibiotic of formula 2 is selected from ristocetin A and ristocetin A pseudoaglycone.

8. A compound of formula 3:

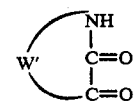

3 wherein W' represents the remaining portion of a glycopeptide antibiotic of formula 4:

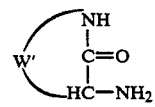

4 the formula 4 antibiotic being selected from A35512 factors A, B, C, E and H, A35512B pseudoaglycone, A41030 factors A, B, C, D, E, F and G, A47934, ristocetin A and ristocetin A pseudoaglycone, or a salt thereof.

9. A compound of claim 8 wherein the salt is pharmaceutically acceptable.

10. A compound of claim 8 wherein the antibiotic of formula 4 is A47934.

11. A compound of claim 8 wherein the antibiotic of formula 4 is selected from A35512B factors A, B, C, E and H and A35512B pseudoaglycone.

12. A compound of claim 8 wherein the antibiotic of formula 4 is selected from actaplanin factors A, B$_1$, B$_2$, B$_3$, C$_{1a}$, C$_{2a}$, C$_3$, D$_1$, D$_2$, E$_1$, G, K, L, M, N and O and actaplanin pseudoaglycone.

13. A compound of claim 8 wherein the antibiotic of formula 4 is selected from A41030 factors A, B, C, D, E, F and G.

14. A compound of claim 8 wherein the antibiotic of formula 4 is selected from ristocetin A and ristocetin A pseudoaglycone.

15. A pharmaceutical composition for treating gram-positive bacterial infections which comprises an effective amount of a compound of claim 8, or a pharmaceutically acceptable salt thereof, and a suitable pharmaceutical vehicle.

16. A method of treating susceptible gram-positive bacterial infections which comprises administering an effective amount of a composition of claim 15 to an infected or susceptible warm-blooded animal.

17. A feed composition for increasing feed-utilization efficiency in animals which comprises (1) an effective amount of a compound of claim 8, or a pharmaceutically-acceptable salt thereof, and (2) a standard feed ration.

18. A method for increasing feed-utilization in animals which comprises administering an effective amount of a composition of claim 17 to the animal.

19. A feed composition for improving milk production in lactating ruminants comprising (1) an effective amount of a compound of claim 8, or a pharmaceutically acceptable salt thereof and (2) a standard feed ration.

20. A method for improving milk production in lactating ruminants comprising orally administering an effective amount of a composition of claim 19 to the ruminant.

21. The method of claim 20 wherein the ruminant is a dairy cow.

* * * * *

Disclaimer 4,504,467.—*R. Michael Molloy*, Danville and *Manuel Debono*, Indianapolis, Ind. GLYCOPEPTIDE DERIVATIVES. Patent dated Mar. 12, 1985. Disclaimer filed Jan. 14, 1986, by the assignee, *Eli Lilly and Co.*

Hereby enters this disclaimer to claim 12 of said patent.
[*Official Gazette March 11, 1986.*]